United States Patent [19]

Chang et al.

[11] 4,418,155

[45] Nov. 29, 1983

[54] CONVERSION OF SYNTHESIS GAS TO HYDROCARBONS ENRICHED IN LINEAR ALPHA-OLEFINS

[75] Inventors: Clarence D. Chang, Princeton; William H. Lang, Pennington, both of N.J.

[73] Assignee: Mobil Oil Corporation, New York, N.Y.

[21] Appl. No.: 133,384

[22] Filed: Mar. 24, 1980

[51] Int. Cl.$^3$ .................................................. C07C 1/04
[52] U.S. Cl. ...................................... 518/719; 518/715; 518/720
[58] Field of Search .................... 260/449.6 R, 449 R; 518/715, 717, 719, 720

[56] References Cited

U.S. PATENT DOCUMENTS

| | | | |
|---|---|---|---|
| 4,049,734 | 9/1977 | Garwood et al. | 260/449 R X |
| 4,086,262 | 4/1978 | Chang et al. | 260/449.6 R |
| 4,157,338 | 6/1979 | Haag et al. | 260/449 R |
| 4,172,843 | 10/1979 | Dwyer et al. | 260/449.6 R |
| 4,207,248 | 6/1980 | Butter et al. | 260/449.6 R |
| 4,207,250 | 6/1980 | Butter et al. | 260/449.6 R |

*Primary Examiner*—Howard T. Mars
*Attorney, Agent, or Firm*—Alexander J. McKillop; Michael G. Gilman; Charles J. Speciale

[57] ABSTRACT

A method is disclosed for converting synthesis gas to hydrocarbons enriched in linear alpha-olefins which involves the use of a ZSM-5 type zeolite which is substantially catalytically inert and onto which is deposited a carbon oxide reducing component including Fischer-Tropsch type catalysts, such as iron, cobalt and ruthenium.

5 Claims, No Drawings

CONVERSION OF SYNTHESIS GAS TO HYDROCARBONS ENRICHED IN LINEAR ALPHA-OLEFINS

BACKGROUND OF THE INVENTION

1. Field of the Invention

This invention is concerned with an improved process for converting synthesis gas, i.e. mixtures of gaseous carbon oxides with hydrogen or hydrogen donors, to hydrocarbon mixtures enriched in linear alpha-olefins utilizing a catalytically inactive (i.e. substantially non-acidic) zeolite of the ZSM-5 type onto which is deposited a carbon oxide reducing component such as iron.

Processes for the conversion of coal and other hydrocarbons, such as natural gas, to a gaseous mixture consisting essentially of hydrogen and carbon monoxide and/or dioxide are well known. Those of major importance depend either on the partial combustion of the fuel with an oxygen-containing gas or on the high temperature reaction of the fuel with steam, or on a combination of these two reactions. An excellent summary of the art of gas manufacture, including synthesis gas, from solid and liquid fuels is given in Encyclopedia of Chemical Technology, edited by Kirk-Othmer, Second Edition, Volume 10, pages 353–433 (1966), Interscience Publishers, New York, N.Y.

It is also well known that synthesis gas will undergo conversion to reduction products of carbon monoxide, such as hydrocarbons, at from about 300° F. to about 850° F., under from about one to one thousand atmospheres pressure, over a fairly wide variety of catalysts. The Fischer-Tropsch process, for example, which has been most extensively studied, produces a range of liquid hydrocarbons, a portion of which have been used as low octane gasoline. Catalysts that have been studied for this and related processes include those based on iron, cobalt, nickel, ruthenium, thorium, rhodium and osmium, or their oxides.

Recently, it has been discovered that the conversion of synthesis gas into valuable products can be greatly enhanced by employing a special type of crystalline aluminosilicate zeolite exemplified by ZSM-5 in admixture with a carbon monoxide reduction catalyst. Thus, for example, in U.S. Pat. No. 4,086,262, there is disclosed a process for the conversion of syngas by passing the same at elevated temperature over a catalyst which comprises an intimate mixture of a Fischer-Tropsch component and a special type of zeolite such as ZSM-5. Said patent points out that the products produced are hydrocarbon mixtures which are useful in the manufacture of heating oil, high octane gasoline, aromatic compounds, and chemical intermediates.

Although U.S. Pat. No. 4,086,262 is primarily directed to multi-practice composite catalysts, i.e. the crystalline aluminosilicate component (one particle) is physically admixed with the Fisher-Tropsch component (another particle), nevertheless, Example 5 of said patent does disclose an iron-impregnated ammonium exchanged ZSM-5 in an alumina matrix.

As can well be appreciated, the patent and technical literature relating to the Fischer-Tropsch process, is, indeed, extensive and the various catalysts reported in the prior art have been used by themselves as well as in admixture with catalytically inactive supports such as kieselguhr. Although the reasons for using catalytically inactive supports have varied, nevertheless, it would appear that one reason for using the same was that it resulted in increased surface area of the Fischer-Tropsch component upon which it was deposited or admixed and that it also aided in controlling the heat-requirements of the overall exothermic reactions.

CROSS REFERENCE TO RELATED CASES

This application is related to Ser. No. 926,987 filed July 21, 1978 and now U.S. Pat. No. 4,172,843.

DESCRIPTION OF PREFERRED EMBODIMENTS

The novel process of this invention is directed towards an improvement in the process of converting syngas to a very specific product; namely, one that is enriched in linear alphaolefins. As has heretofore been stated, the concept of contacting syngas with ZSM-5 type zeolites containing carbon oxide reducing components is old in the art. In this connection, U.S. Pat. No. 4,086,262, previously referred to, as well as U.S. Pat. No. 4,096,163 disclosed processes for conversion of syngas utilizing ZSM-5 type zeolites in admixture with carbon oxide reducing components, such as Fischer-Tropsch materials.

However, all the heretofore mentioned prior art involve the use of ZSM-5 type zeolites which were catalytically active i.e. were acidic. As is well known in the art, the use of an acidic material results in the ability to be able to catalyze the transformation of hydrocarbons into different products.

The instant invention is concerned with a substantially catalytically inactive support and is directed towards the concept of using the particular pore diameters of a ZSM-5 type zeolite in order to direct the conversion of syngas to a particular product; namely, one which is enriched in linear alpha-olefins. Thus, this invention is not at all concerned with conventional acidic catalysis, but rather, is concerned with the use of substantially catalytically inactive materials which influence the selectivity or course of reactions when used as a catalyst support for carbon oxide reducing materials such as Fischer-Tropsch components.

The novel process of this invention enhances the selectivity of the product to linear alpha-olefins, in general, and more particularly to $C_4$–$C_6$ olefins. Linear alpha-olefins are very valuable products and can be used in a wide variety of chemical processes as is well known in the art, such as the production of soaps, lubricating oils, etc.

Another significant difference between the novel process of this invention and the heretofore practiced processes for the conversion of syngas involving ZSM-5 type zeolite resides in the fact that the specific products will not be obtained if physical mixtures of ZSM-5 and carbon oxide reducing components are used. In the vast majority of Fischer-Tropsch conversion processes involving ZSM-5 type zeolites, mixtures of discrete particles are utilized in order to effect the transformation of a syngas into various products, either enriched in olefins or enriched in aromatics. As will be demonstrated later on by specific examples, in order to obtain the novel distribution of linear alpha-olefins in the process of this invention, it is necessary that the carbon oxide reducing components, i.e. iron, cobalt or ruthenium, be present within the pores of the ZSM-5 type zeolite. In this connection, methods for including carbon oxide reducing components within the pores of ZSM-5 type zeolites are known in the art and the preferred technique involves impregnation of the zeolite with an aqueous solution of a salt of the desired metal. The nature of the salt is not critical and any water-soluble salt such as the chloride, sulfate, and nitrate can be utilized although in the examples which follow, the nitrate was the salt employed.

The expression ZSM-5 type zeolites as used throughout the specification and claims is intended to include zeolite ZSM-5, ZSM-11, ZSM-12, ZSM-35, or ZSM-38, as well as all materials having the x-ray diffraction pattern of these zeolites irrespective of chemical composition.

ZSM-5 is more fully described in U.S. Pat. No. 3,702,886, the disclosure of which is herein incorporated by reference.

ZSM-11 is more particularly described in U.S. Pat. No. 3,702,979, the entire contents of which are herein incorporated by reference.

ZSM-12 is more particularly described in U.S. Pat. No. 3,832,449, the entire contents of which are being incorporated by reference.

ZSM-35 is described in U.S. Pat. No. 4,016,245 and ZSM-38 is described in U.S. Pat. No. 4,046,859, both of which are incorporated herein by reference.

As has heretofore been stated, it is essential to the novel process of this invention that the ZSM-5 type zeolite be substantially catalytically inert so that it will perform a sieving function only as opposed to a catalytic transformation of the hydrocarbons produced from syngas conversion. Another way of stating the same thing is to say that the ZSM-5 type zeolite should be substantially non-acidic. In order to obtain this condition, various techniques can be utilized. It is known in the art that the greater the aluminum content of a ZSM-5 type zeolite which is present in the skeletal structure, the greater opportunity there is to have exchangable sights which can be acidic. Conversely, the lower the aluminum content the less availability there is to provide acid sites via base exchange or other techniques. Therefore, if the ZSM-5 type zeolite which is used is substantially free of alumina, i.e. a silica to alumina ratio of greater than about 1600, then no particular caution ordinarily need be taken and such material can be utilized in the "as synthesized state" for the reason that these materials simply do not have sufficient inherent acidity to be catalytically active under the reaction conditions of this invention. On the other hand, if ZSM-5 type zeolites of fairly high alumina content are utilized, i.e. silica-to-alumina ratios less than 1600, special precautions must be taken to ensure that the zeolite is substantially catalytically inert. In this connection, the zeolite can be base exchanged with alkali metal cations, preferably sodium, in order to substantially eliminate all acidity.

In this connection, a special test has been devised to measure the acidity of various candidate catalysts in order to determine whether or not they are operable in the novel process of this invention. The test involves measure of the rate of cyclopropane isomerization and comparing it against 46 A.I. silica-alumina as a reference standard.

The test procedure involves utilizing a 5 to 250 mg. sample having a particle size of 20 to −200 mesh and mixing the same with about 1 ml of Vycor chips and loading into a 5 mm inside diameter Vycor reactor tube which is heated in air at a flow rate of 150 ml per minute to 538° C. and maintained there for 30 minutes. The sample is then cooled to 250° C. in helium at a flow rate of 12-80 ml per minute. Cyclopropane (helium/cyclopropane, 4, vol. to vol.) is then introduced and the reactor effluent analyzed by gas chromatographic techniques. The contact time is adjusted to keep the conversion with 0.5 to 50%. Since it is well known in the literature that the isomerization of cyclopropane is first order, rate constants may be determined at several temperatures to check for diffusion limitations. Using the above technique, the first order rate content for the standard 46 A.I. silica-alumina catalyst is 63.3 seconds$^{-1}$ at 250° C. This value was arbitrarily assigned an index of 1,000 so as to serve as a reference value. Thus, the cyclopropane index (C.P.I Index) for a candidate catalyst with a first order rate constant of 0.633 would be determined as follows:

$$(1,000 \times 0.633)/63.3 = 10$$

Thus, the expression "substantially catalytically inert" as used throughout the specification and claims is intended to define a zeolite which has a C.P.I. Index of no greater than 10 as measured by the aforementioned test.

The following table lists the values obtained when subjecting various materials, including crystalline aluminosilicate zeolites, to the cyclopropane isomerization test previously set forth.

TABLE 1

| | Cyclopropane Isomerization (CPI) Index | | |
|---|---|---|---|
| | Materials | k, sec$^{-1}$ 250° C. | CPI |
| 1. | MgPHZSM-5 | 151 | 2400 |
| 2. | 46 A.I. Si/Al, Ref. Std. | 63.3 | 1000 |
| 3. | ZrO$_2$ | 60.2 | 950 |
| 4. | HZSM-5, SiO$_2$/Al$_2$O$_3$ = 1670 | 50.0 | 790 |
| 5. | KHZSM-5 | 3.98 | 63 |
| 6. | NaZSM-5, SiO$_2$/Al$_2$O$_3$ = 70 (exchanged with NaHCO$_3$) | 1.36 | 21 |
| 7. | NaHZSM-5, SiO$_2$/Al$_2$O$_3$ = 1670 | 0.441 | 7.0 |
| 8. | NaZSM-5, SiO$_2$/Al$_2$O$_3$ = 600 | 0.125 | 2.0 |
| 9. | NaZSM-5, SiO$_2$/Al$_2$O$_3$ = 1670 | 0.050 | 0.8 |
| 10. | FeNaZSM-5, SiO$_2$/Al$_2$O$_3$ = 1600 | 0.021 | 0.3 |

From the above table, it can be seen that there are ZSM-5 zeolites which are operable in the novel process of this invention, i.e. have a C.P.I. Index of no greater than 10, as well as ZSM-5 type materials which are inoperable in the process of this invention. Thus, for example, Material No. 1 is a magnesium phosphorous exchanged ZSM-5 and, as can be seen, its acidity is higher than the 46 A.I. reference standard. Material No. 4 is an acid exchanged ZSM-5 zeolite having a silica-to-alumina ratio of 1670 and, as can be seen, this material is also inoperable in the novel process of this invention. Material No. 5 is a potassium exchanged acid ZSM-5 and Catalyst No. 6 is a sodium exchanged ZSM-5, but they simply have not been exchanged with enough alkali metal to lower their acidity. Materials 7, 8, 9 and 10 would all posess a sufficiently low C.P.I. Index to be potential candidates for the novel process of this invention, providing of course that a Fischer-Tropsch component had been introduced within the pores thereof. In this connection, Catalyst No. 10 is the very material which was tested in Example 1.

The novel process of this invention is carried out at temperatures ranging from about 500° to 650° F. and more preferably from 550° to about 600° F. The novel process of this invention is carried out at gas hourly space velocities (GHSV), ranging from 400 to 20,000 and more desirably from 500 to 6,000, based on fresh feed and total catalyst volume. Hydrogen to carbon oxides ratios can vary from 0.5:1 to 2:1 and more preferably are about 1:1, pressures ranging from 50 to 1,000 psig and more preferably from 150 to 400 psig are employed.

The following examples will illustrate the novel process of this invention.

EXAMPLES 1–8

In Examples 1–8 various materials were evaluated for the conversion of synthesis gas as follows:

Example 1—ZSM-5 having a $SiO_2/Al_2O_3$ ratio of about 1600 and a sodium content of about 1.6 weight percent impregnated with an aqueous solution of iron nitrate to 1.0 weight percent iron.

Example 2—Same as Example 1, except that 1 weight percent of potassium is added.

Example 3—Sodium mordenite having a $SiO_2/Al_2O_3$ ratio of 93 and a sodium content of 1.7 weight percent impregnated with an aqueous solution of iron nitrate to 1.0 weight percent iron.

Example 4—$SiO_2$ (Girdler T-1571) and magnetite sized to 10/30 mesh and containing 10 weight percent iron.

Example 5—ZSM-5 base exchanged with ammonium ions and containing 0.95 weight percent potassium physically admixed with iron in the ratio of 1.03 grams TEK and 0.88 grams ZSM-5.

Example 6—ZSM-5 having a $SiO_2/Al_2O_3$ ratio of about 70 partially base exchanged with sodium and impregnated with an aqueous solution of iron nitrate to 1.0 weight percent iron.

Example 7—Same ZSM-5 as Example 1 but physically admixed with magnetite so as to contain 1 weight percent iron.

Example 8—Same ZSM-5 as Example 1 but impregnated with iron nitrate to 10 weight percent iron.

Conversion of syngas ($H_2/CO=1$) was carried out over the above catalysts at 400–800 psig, 288°–316° C. and 520–740 GHSV. The results obtained are shown in Table 2.

TABLE 2

| | SYNGAS CONVERSION TO LINEAR ALPHA OLEFINS (LAO) | | | | | | | |
|---|---|---|---|---|---|---|---|---|
| Example | 1 | 2 | 3 | 4 | 5 | 6 | 7 | 8 |
| Catalyst Support | NaZSM-5 | NaKZSM-5 | Na—Mordenite | $SiO_2$ | KHZSM-5 | NAHZSM-5 | NaZSM-5 | NaZSM-5 |
| CPI Index | 0.3 | 0.4 | 9.1 | 6.2 | 63.0 | 11.0 | 0.3 | 0.3 |
| Conversion, % | 22 | 10 | 55 | 32 | 78 | 25 | 11.8 | 53.8 |
| Product Distribution, % | | | | | | | | |
| Methane | 6.67 | 6.22 | 13.55 | 24.72 | 18.00 | 13.24 | 18.08 | 6.25 |
| $C_2^+$ Paraffins | 18.01 | 19.21 | 29.88 | 37.88 | 29.19 | 50.39 | 29.43 | 22.80 |
| Linear alpha olefins | 48.25 | 67.04 | 37.01 | 16.34 | 4.77 | 5.06 | 26.82 | 45.08 |
| Other olefins | 3.18 | 3.82 | 17.14 | 17.48 | 40.56 | 26.59 | 9.34 | 4.58 |
| Aromatics | — | — | — | 0.76 | 8.48 | 4.71 | — | — |
| Alcohols | 13.34 | 3.77 | 2.10 | 2.82 | — | 0.01 | 16.33 | 16.67 |
| Carbonyl Compounds | 10.55 | 0.84 | 0.32 | — | — | — | — | 4.62 |
| % LAO in Olefins | 93.8 | 94.6 | 68.2 | 48.3 | 10.5 | 16.0 | 74.2 | 90.8 |

As can be seen from Table 2, only the catalysts of Examples 1, 2 and 8 were able to significantly enhance the product in linear aliphatic olefins. Mordenite catalyst (Example 3) did not enhance the product in linear alpha olefins as well as Examples 1, 2 and 8, even though its C.P.I. Index was low.

Example 7 vividly demonstrates the criticality of having the iron in the pores as evidenced by decreased linear alpha olefins and increased methane.

Examples 4, 5 and 6 are obviously inferior. Example 8 shows that the concentration of iron is not narrowly critical.

Complete product distribution for Examples 1, 2, 3, 4, 6, 7 and 8 are shown in the following Tables.

TABLE 3

| | Product Distribution of Example 1 | | | | | | | |
|---|---|---|---|---|---|---|---|---|
| Carbon No. | n-paraffins | Isoparaffins | Linear α-Olefins | Other Olefins | Alcohols | Aldehydes | Ketones | Acids |
| 1 | 6.67 | — | — | — | 4.10 | trace | — | |
| 2 | 1.86 | — | 4.66 | — | 4.40 | trace | | |
| 3 | 1.86 | — | 8.55 | — | 1.06 | 0.18 | | |
| 4 | 1.70 | trace | 6.12 | 0.50 | .76 | .73 | | |
| 5 | 1.34 | trace | 3.77 | .29 | .69 | .81 | | |
| 6 | 1.90 | | 3.84 | .19 | .66 | 1.28 | | |
| 7 | 1.34 | | 3.00 | .18 | .51 | 1.32 | | |
| 8 | 1.11 | | 2.53 | .15 | .37 | 1.25 | | |
| 9 | .80 | | 2.09 | .27 | .45 | 1.06 | | |
| 10 | .71 | | 2.04 | .27 | .14 | 1.05 | | |
| 11 | .66 | | 1.94 | .25 | .11 | .81 | | |
| 12 | .64 | | 1.68 | .18 | .09 | .68 | | |
| 13 | .50 | | 1.43 | .20 | | .61 | | |
| 14 | .43 | | 1.29 | .16 | | .39 | | |
| 15 | .34 | | 1.19 | .16 | | .26 | | |
| 16 | .56 | | 1.01 | .15 | | .12 | | |
| 17 | .75 | | 1.21 | .10 | | | | |
| 18 | .49 | | .68 | .08 | | | | |
| 19 | .45 | | .53 | .05 | | | | |
| 20 | .37 | | .49 | | | | | |
| 21 | .20 | | .20 | | | | | |
| 22 | trace | | | | | | | |
| 23 | | | | | | | | |

TABLE 3-continued

Product Distribution of Example 1

| Carbon No. | n-paraffins | Isoparaffins | Linear α-Olefins | Other Olefins | Alcohols | Aldehydes | Ketones | Acids |
|---|---|---|---|---|---|---|---|---|
| 24 | | | | | | | | |
| 25 | | | | | | | | |
| 26 | | | | | | | | |
| 27 | | | | | | | | |
| 28 | | | | | | | | |
| 29 | | | | | | | | |
| 30 | | | | | | | | |
| Total | 24.68 | trace | 48.25 | 3.18 | 13.34 | | 10.55 | |

Other Compounds

| Aromatics | Naphthenes |
|---|---|
| 0 | 0 |

TABLE 4

Product Distribution of Example 2

| Carbon No. | n-paraffins | Isoparaffins | Linear α-Olefins | Other Olefins | Alcohols | Aldehydes | Ketones | Acids |
|---|---|---|---|---|---|---|---|---|
| 1 | 6.22 | — | — | — | 0.34 | | | |
| 2 | .91 | — | 5.17 | — | .52 | | | |
| 3 | 1.61 | — | 9.43 | — | .20 | | | |
| 4 | 1.12 | trace | 5.94 | 0.98 | .32 | | | |
| 5 | .21 | | 2.95 | .28 | .55 | | 0.06 | |
| 6 | .52 | | 1.95 | .21 | .15 | 0.08 | .10 | |
| 7 | .61 | | 2.12 | .26 | .34 | .12 | .07 | |
| 8 | 1.29 | | 2.81 | .19 | .34 | .08 | .08 | |
| 9 | 1.06 | | 3.91 | .35 | .19 | .06 | .08 | |
| 10 | .93 | | 2.57 | .27 | .29 | .06 | | |
| 11 | .80 | | 2.94 | .06 | .22 | .05 | | |
| 12 | .86 | | 3.05 | .15 | .17 | | | |
| 13 | 1.10 | | 2.96 | .18 | .12 | | | |
| 14 | 1.03 | | 2.80 | .17 | .01 | | | |
| 15 | .75 | | 2.59 | .13 | .01 | | | |
| 16 | .66 | | 2.33 | .18 | | | | |
| 17 | .62 | | 2.18 | .17 | | | | |
| 18 | .66 | | 1.99 | .06 | | | | |
| 19 | .61 | | 1.88 | .08 | | | | |
| 20 | .59 | | 1.68 | .04 | | | | |
| 21 | .55 | | 1.36 | .03 | | | | |
| 22 | .49 | | 1.28 | .03 | | | | |
| 23 | .43 | | 1.06 | | | | | |
| 24 | .36 | | .75 | | | | | |
| 25 | .29 | | .70 | | | | | |
| 26 | .25 | | .64 | | | | | |
| 27 | trace | | | | | | | |
| 28 | | | | | | | | |
| 29 | | | | | | | | |
| 30 | | | | | | | | |
| Total | 25.43 | trace | 67.04 | 3.82 | 3.77 | 0.45 | 0.39 | |

Other Compounds

| Aromatics | Naphthenes |
|---|---|
| 0 | 0 |

TABLE 5

Product Distribution of Example 3

| Carbon No. | n-paraffins | Isoparaffins | Linear α-Olefins | Other Olefins | Alcohols | Aldehydes | Ketones | Acids |
|---|---|---|---|---|---|---|---|---|
| 1 | 13.55 | — | — | — | 0.46 | | | |
| 2 | 9.48 | — | 3.39 | — | .74 | | | |
| 3 | 4.73 | — | 15.32 | — | .10 | | | |
| 4 | 3.35 | 0.20 | 7.29 | 5.78 | .07 | | | |
| 5 | 2.49 | .23 | 4.05 | 2.46 | .11 | | 0.12 | |
| 6 | 1.67 | .18 | 1.95 | 2.72 | .13 | | .14 | |
| 7 | 1.91 | .20 | 1.46 | 2.23 | .16 | | | |
| 8 | 1.14 | .12 | .92 | 1.30 | .13 | | | |
| 9 | .84 | .08 | .74 | .78 | .07 | | .06 | |
| 10 | .56 | .05 | .52 | .57 | .05 | | | |
| 11 | .46 | .05 | .39 | .35 | .02 | | | |
| 12 | .48 | .05 | .31 | .27 | .01 | | | |
| 13 | .34 | .04 | .26 | .23 | | | | |
| 14 | .29 | .03 | .14 | .21 | | | | |
| 15 | .26 | .02 | .10 | .10 | | | | |
| 16 | .23 | .02 | .08 | .10 | | | | |
| 17 | .19 | .02 | .06 | .04 | | | | |

TABLE 5-continued

Product Distribution of Example 3

| Carbon No. | n-paraffins | Isoparaffins | Linear α-Olefins | Other Olefins | Alcohols | Aldehydes | Ketones | Acids |
|---|---|---|---|---|---|---|---|---|
| 18 | .08 | .01 | .03 | | | | | |
| 19 | .03 | | | | | | | |
| 20 | .02 | | | | | | | |
| 21 | .02 | | | | | | | |
| 22 | .01 | | | | | | | |
| 23 | | | | | | | | |
| 24 | | | | | | | | |
| 25 | | | | | | | | |
| 26 | | | | | | | | |
| 27 | | | | | | | | |
| 28 | | | | | | | | |
| 29 | | | | | | | | |
| 30 | | | | | | | | |
| Total | 42.13 | 1.30 | 37.01 | 17.14 | 2.10 | | 0.32 | |

Other Compounds

| Aromatics | Naphthenes |
|---|---|
| 0 | 0 |

TABLE 6

Product Distribution of Example 4

| Carbon No. | n-paraffins | Isoparaffins | Linear α-Olefins | Other Olefins | Alcohols | Aldehydes | Ketones | Acids |
|---|---|---|---|---|---|---|---|---|
| 1 | 24.72 | — | — | — | 1.48 | | | |
| 2 | 9.01 | — | 2.72 | — | 1.05 | | | |
| 3 | 6.84 | — | 10.32 | — | 0.29 | | | |
| 4 | 3.95 | 0.31 | 1.77 | 6.16 | trace | | | |
| 5 | 2.73 | .53 | .59 | 4.43 | | | | |
| 6 | 1.80 | .82 | .31 | 2.93 | | | | |
| 7 | 1.70 | .81 | .13 | 1.45 | | | | |
| 8 | 1.40 | 1.06 | .20 | 1.33 | | | | |
| 9 | 1.04 | 1.36 | .14 | .70 | | | | |
| 10 | .81 | 1.13 | .22 | .39 | | | | |
| 11 | .49 | .84 | .21 | .25 | | | | |
| 12 | .33 | .60 | .20 | .14 | | | | |
| 13 | .26 | .48 | | .14 | | | | |
| 14 | .12 | .12 | | .03 | | | | |
| 15 | .08 | .06 | | .02 | | | | |
| 16 | .04 | .03 | | .01 | | | | |
| 17 | .02 | .01 | | .01 | | | | |
| 18 | .01 | trace | | | | | | |
| 19 | .01 | | | | | | | |
| 20 | trace | | | | | | | |
| 21 | | | | | | | | |
| 22 | | | | | | | | |
| 23 | | | | | | | | |
| 24 | | | | | | | | |
| 25 | | | | | | | | |
| 26 | | | | | | | | |
| 27 | | | | | | | | |
| 28 | | | | | | | | |
| 29 | | | | | | | | |
| 30 | | | | | | | | |
| Total | 53.80 | 7.93 | 16.34 | 17.48 | 2.82 | | | |

Other Compounds

| Aromatics | Naphthenes |
|---|---|
| 0.76 | 0.87 |

TABLE 7

Product Distribution of Example 6

| Carbon No. | n-paraffins | Isoparaffins | Linear α-Olefins | Other Olefins | Alcohols | Aldehydes | Ketones | Acids |
|---|---|---|---|---|---|---|---|---|
| 1 | 13.24 | — | — | — | 0.01 | | | |
| 2 | 5.88 | — | 2.40 | — | | | | |
| 3 | 3.51 | — | 2.29 | — | | | | |
| 4 | 3.14 | 2.01 | 0.37 | 7.79 | | | | |
| 5 | 1.55 | 2.19 | trace | 7.43 | | | | |
| 6 | 1.73 | 4.46 | | 6.12 | | | | |
| 7 | 1.74 | 3.13 | | 2.89 | | | | |
| 8 | 1.79 | 2.86 | | .42 | | | | |
| 9 | 1.60 | 2.95 | | .47 | | | | |
| 10 | .86 | 1.87 | | .41 | | | | |
| 11 | .75 | 1.44 | | .46 | | | | |

TABLE 7-continued

Product Distribution of Example 6

| Carbon No. | n-paraffins | Isoparaffins | Linear α-Olefins | Other Olefins | Alcohols | Aldehydes | Ketones | Acids |
|---|---|---|---|---|---|---|---|---|
| 12 | .33 | .80 |  | .20 |  |  |  |  |
| 13 | .39 | .96 |  | .21 |  |  |  |  |
| 14 | .25 | .57 |  | .13 |  |  |  |  |
| 15 | .12 | .31 |  | .04 |  |  |  |  |
| 16 | .05 | .17 |  | .02 |  |  |  |  |
| 17 | .04 | .16 |  | trace |  |  |  |  |
| 18 | .03 | .13 |  |  |  |  |  |  |
| 19 | .03 | .09 |  |  |  |  |  |  |
| 20 | .03 | .10 |  |  |  |  |  |  |
| 21 | .03 | .09 |  |  |  |  |  |  |
| 22 | .02 | .09 |  |  |  |  |  |  |
| 23 | .02 | .05 |  |  |  |  |  |  |
| 24 | .01 | .04 |  |  |  |  |  |  |
| 25 | .02 | .06 |  |  |  |  |  |  |
| 26 | .05 | .15 |  |  |  |  |  |  |
| 27 | .06 | .19 |  |  |  |  |  |  |
| 28 | .08 | .23 |  |  |  |  |  |  |
| 29 | .07 | .22 |  |  |  |  |  |  |
| 30 | .19 | .70 |  |  |  |  |  |  |
| Total | 37.61 | 26.02 | 5.06 | 26.59 | 0.01 |  |  |  |

| Other Compounds | |
|---|---|
| Aromatics | Naphthenes |
| 4.71 | 0 |

TABLE 8

Product Distribution of Example 7

| Carbon No. | n-paraffins | Isoparaffins | Linear α-Olefins | Other Olefins | Alcohols | Aldehydes | Ketones | Acids |
|---|---|---|---|---|---|---|---|---|
| 1 | 18.08 | — | — | — | 2.88 |  |  |  |
| 2 | 7.47 | — | 4.14 | — | 7.06 |  |  |  |
| 3 | 4.45 | — | 9.16 | — | 2.77 |  |  |  |
| 4 | 2.98 | 0.20 | 4.35 | 1.40 | 1.27 |  |  |  |
| 5 | 1.99 | .11 | 2.93 | .36 | .59 |  |  |  |
| 6 | 1.01 | .47 | 1.37 | .88 | .39 |  |  |  |
| 7 | .88 | .46 | 1.01 | .88 | .33 |  |  |  |
| 8 | .96 | .44 | .95 | 1.21 | .37 |  |  |  |
| 9 | .98 | .65 | .72 | 1.17 | .36 |  |  |  |
| 10 | .94 | .65 | .51 | 1.13 | .24 |  |  |  |
| 11 | .78 | .54 | .38 | .83 | .03 |  |  |  |
| 12 | .64 | .36 | .29 | .69 | .02 |  |  |  |
| 13 | .51 | .26 | .29 | .42 | .02 |  |  |  |
| 14 | .31 | .20 | .23 | .13 |  |  |  |  |
| 15 | .26 | .07 | .16 | .08 |  |  |  |  |
| 16 | .21 | .03 | .11 | .05 |  |  |  |  |
| 17 | .20 | .03 | .08 | .03 |  |  |  |  |
| 18 | .15 | .03 | .07 | .03 |  |  |  |  |
| 19 | .11 | .02 | .05 | trace |  |  |  |  |
| 20 | .05 | trace | .02 |  |  |  |  |  |
| 21 | .03 |  |  |  |  |  |  |  |
| 22 | trace |  |  |  |  |  |  |  |
| 23 |  |  |  |  |  |  |  |  |
| 24 |  |  |  |  |  |  |  |  |
| 25 |  |  |  |  |  |  |  |  |
| 26 |  |  |  |  |  |  |  |  |
| 27 |  |  |  |  |  |  |  |  |
| 28 |  |  |  |  |  |  |  |  |
| 29 |  |  |  |  |  |  |  |  |
| 30 |  |  |  |  |  |  |  |  |
| Total | 42.99 | 4.52 | 26.82 | 9.34 | 16.33 |  |  |  |

| Other Compounds | |
|---|---|
| Aromatics | Naphthenes |

TABLE 9

Product Distribution of Example 8

| Carbon No. | n-paraffins | Isoparaffins | Linear α-Olefins | Other Olefins | Alcohols | Aldehydes | Ketones | Acids |
|---|---|---|---|---|---|---|---|---|
| 1 | 6.25 | — | — | — | 1.13 |  |  |  |
| 2 | 3.96 | — | 5.93 | — | 2.92 |  | 0.02 |  |
| 3 | 2.71 | 0.18 | 9.60 | — | 1.55 |  | .14 |  |
| 4 | 1.63 | .16 | 5.44 | 0.66 | 2.09 |  | .30 |  |
| 5 | 1.13 | .36 | 3.15 | .18 | 2.28 |  | .43 |  |
| 6 | 1.00 | .14 | 2.34 | .11 | 1.58 |  | .34 |  |

TABLE 9-continued

Product Distribution of Example 8

| Carbon No. | n-paraffins | Isoparaffins | Linear α-Olefins | Other Olefins | Alcohols | Aldehydes | Ketones | Acids |
|---|---|---|---|---|---|---|---|---|
| 7 | .76 | .17 | 3.09 | .09 | 1.01 | | .35 | |
| 8 | 1.09 | .18 | 3.22 | .18 | .69 | | .35 | |
| 9 | .76 | .29 | 2.85 | .37 | .63 | | 1.74 | |
| 10 | 1.09 | .23 | 2.58 | .34 | .52 | | .18 | |
| 11 | 1.19 | .12 | 1.84 | .47 | .49 | | .17 | |
| 12 | 1.18 | .18 | 1.40 | .45 | .37 | | .15 | |
| 13 | 1.16 | | 1.04 | .43 | .18 | | .14 | |
| 14 | 1.02 | | .81 | .39 | .08 | | .12 | |
| 15 | .85 | | .63 | .37 | .01 | | .09 | |
| 16 | .73 | | .47 | .29 | | | .07 | |
| 17 | .64 | | .35 | .18 | | | .03 | |
| 18 | .56 | | .30 | .05 | | | | |
| 19 | .47 | | .10 | | | | | |
| 20 | .34 | | .04 | | | | | |
| 21 | .23 | | | | | | | |
| 22 | .12 | | | | | | | |
| 23 | .02 | | | | | | | |
| 24 | trace | | | | | | | |
| 25 | | | | | | | | |
| 26 | | | | | | | | |
| 27 | | | | | | | | |
| 28 | | | | | | | | |
| 29 | | | | | | | | |
| 30 | | | | | | | | |
| Total | 27.04 | 2.01 | 45.08 | 4.58 | 16.67 | | 4.62 | |
| Other Compounds | | | | | | | | |
| Aromatics | Naphthenes | | | | | | | |

EXAMPLES 9-10

The following examples will illustrate the use of ruthenium as the carbon oxide reducing component. In Example 9, the same ZSM-5 zeolite having a silica-to-alumina ratio of about 1600 and a sodium content of about 1.6 as was utilized for the preparation of the catalyst of Example 1 was impregnated with an aqueous solution of ruthenium nitrate, followed by calcination overnight at 1000° F. and activation with flowing hydrogen at 482° F. at a pressure of 500 psig for two hours. This resulted in obtaining a catalyst containing 0.5% ruthenium.

The catalyst of Example 10 was prepared by subjecting silica to an aqueous impregnation with ruthenium nitrate under identical conditions as in Example 9 so as to obtain a material having a ruthenium content of 0.5 weight percent on silica.

Both materials had a C.P.I. Index less than 10 and were then evaluated for the conversion of syngas (hydrogen gas/CO=2) at 600° F., 500 psig at a GHSV of 420. The results are shown in the following table.

TABLE 10

Effect of Support on Ru F—T Catalysts

| Example Catalyst | 8<br>0.8 Ru on SiO$_2$ | 9<br>0.5% Ru on ZSM-5 |
|---|---|---|
| T°F. | 600 | 600 |
| P, psig | 500 | 500 |
| GHSV, Hr. | 420 | 420 |
| H$_2$/CO | 2 | 2 |
| Conversion, M % | 21.6 | 25.3 |
| Products, wt % | | |
| Alcohols | 10.3 | 6.7 |
| Aldehydes | — | 1.1 |
| Ethers | — | 0.4 |
| Hydrocarbons | 89.7 | 91.8 |
| Hydrocarbon Distrib'n, wt % | | |
| Methane | 43.4 | 2.8 |
| C$_2$+ Paraffins | 47.9 | 27.1 |
| Olefins | 8.7 | 64.1* |
| | 100.0 | 100.0 |

*>95% linear alpha olefins

From the above table 10, it can be seen that even though both catalysts had a C.P.I. Index of less than 10, selectivity of the ZSM-5 catalyst for linear aliphatic olefins is substantially higher than the silica base catalyst. Thus, in order to obtain the novel product of this invention, it is not enough that a material be used that has a low C.P.I. Index but it must also be a ZSM-5 type zeolite in order to provide the selective conversion desired.

The examples also demonstrate another significant advantage of the novel process of this invention, namely, the suppression of methane make. Note that Examples 1, 2, and 8 of Table 2 and Example 9 of Table 10 had significant suppression of methane.

What is claimed is:

1. In the process of catalytically converting synthesis gas to hydrocarbons by contacting the same at elevated temperatures over a catalyst comprising a ZSM-5 type zeolite and a carbon oxide reducing component, the improvement which comprises utilizing a ZSM-5 type zeolite which is substantially catalytically inert and which contains said carbon oxide reducing component in the pores thereof and obtaining a hydrocarbon product enriched in C$_4$-C$_6$ linear alpha olefins.

2. The process of claim 1 wherein said carbon oxide reducing component is iron.

3. The process of claim 1 wherein said carbon oxide reducing component is cobalt.

4. The process of claim 1 wherein said carbon oxide reducing component is ruthenium.

5. The process of claim 1 wherein said zeolite is ZSM-5.

* * * * *